(12) United States Patent
Yap et al.

(10) Patent No.: US 11,360,180 B2
(45) Date of Patent: Jun. 14, 2022

(54) METHODS, SYSTEMS, AND COMPUTER READABLE MEDIA FOR USING A TRAINED ADVERSARIAL NETWORK FOR PERFORMING RETROSPECTIVE MAGNETIC RESONANCE IMAGING (MRI) ARTIFACT CORRECTION

(71) Applicant: The University of North Carolina at Chapel Hill, Chapel Hill, NC (US)

(72) Inventors: Pew-Thian Yap, Chapel Hill, NC (US); Siyuan Liu, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 0 days.

(21) Appl. No.: 17/127,366

(22) Filed: Dec. 18, 2020

(65) Prior Publication Data
US 2021/0190892 A1 Jun. 24, 2021

Related U.S. Application Data

(60) Provisional application No. 62/950,926, filed on Dec. 19, 2019.

(51) Int. Cl.
*G01R 33/565* (2006.01)
*A61B 5/055* (2006.01)

(52) U.S. Cl.
CPC ........ *G01R 33/56509* (2013.01); *A61B 5/055* (2013.01)

(58) Field of Classification Search
CPC .......................... G01R 33/65609; A61B 5/055
See application file for complete search history.

(56) References Cited

U.S. PATENT DOCUMENTS

| 7,034,531 | B1 | 4/2006 | Tuch et al. |
| 7,315,756 | B2 | 1/2008 | Yarnykh et al. |
| 9,891,302 | B2 | 2/2018 | Topgaard et al. |
| 2010/0128797 | A1 | 5/2010 | Dey |
| 2011/0199084 | A1 | 8/2011 | Hasan |
| 2014/0184224 | A1 | 7/2014 | Nevo et al. |
| 2017/0010340 | A1 | 1/2017 | Eichner et al. |

(Continued)

FOREIGN PATENT DOCUMENTS

CN 112488975 A 3/2021

OTHER PUBLICATIONS

Howell et al., "The UNC/UMN Baby Connectome Project (BCP): An overview of the study design and protocol development," NeuroImage, vol. 185, pp. 891-905 (2019).

(Continued)

*Primary Examiner* — Gregory H Curran
(74) *Attorney, Agent, or Firm* — Jenkins, Wilson, Taylor & Hunt, P.A.

(57) ABSTRACT

A method for performing retrospective magnetic resonance imaging (MRI) artifact correction includes receiving, as input, an MRI image having at least one artifact; using a trained adversarial network for performing retrospective artifact correction on the MRI image, wherein the trained adversarial network is trained using unpaired artifact-free MRI images and artifact-containing MRI images; and outputting, by the trained adversarial network, a derivative MRI image related to the input, wherein the at least one artifact is corrected in the derivative MRI image.

17 Claims, 9 Drawing Sheets

(56) References Cited

U.S. PATENT DOCUMENTS

| | | |
|---|---|---|
| 2018/0049665 A1 | 2/2018 | Jeong et al. |
| 2020/0111194 A1* | 4/2020 | Wang .................... G06T 3/4076 |
| 2021/0082092 A1* | 3/2021 | Sargent .................... G06T 1/20 |
| 2021/0199743 A1 | 7/2021 | Yap et al. |

OTHER PUBLICATIONS

Kustner et al., "Retrospective correction of motion-affected MR images using deep learning frameworks," Magn Reson Med, vol. 82, pp. 1527-1540 (2019).

Tamada et al., "Motion Artifact Reduction Using a Convolutional Neural Network for Dynamic Contrast Enhanced MR Imaging of the Liver," Magn Reson Med Sci, vol. 19, pp. 64-76 (Apr. 26, 2019).

Haskell et al., "Network Accelerated Motion Estimation and Reduction (NAMER): Convolutional neural network guided retrospective motion correction using a separable motion model," Magn Reson Med., pp. 1-10 (2019).

Johnson et al., "Conditional generative adversarial network for 3D rigid-body motion correction in MRI," Magn Reson Med., vol. 82, pp. 901-910 (2019).

Duffy et al., "Retrospective correction of motion artifact affected structural MRI images using deep learning of simulated motion," 1st Conference on Medical Imaging with Deep Learning, pp. 1-8 (2018).

Johnson et al., "Motion correction in MRI using deep learning," In Proceedings of the 26th Annual Meeting ISMRM, pp. 1-2 (2018).

Ulyanov et al., "Improved Texture Networks: Maximizing Quality and Diversity in Feed-forward Stylization and Texture Synthesis," arXiv:1701.02096v2, pp. 1-9 (Nov. 6, 2017).

Liu et al., "Unsupervised Image-to-Image Translation Networks," 31st Conference on Neural Information Processing Systems (NIPS 2017), pp. 1-9 (2017).

Jin et al., "Deep Convolutional Neural Network for Inverse Problems in Imaging," IEEE Transactions on Image Processing, vol. 26, No. 9, pp. 4509-4522 (Sep. 2017).

Mao et al., "Least Squares Generative Adversarial Networks," In Proceedings of the IEEE International Conference on Computer Vision (ICCV), pp. 2794-2802 (2017).

Zhu et al., "Toward Multimodal Image-to-Image Translation," 31st Conference on Neural Information Processing Systems (NIPS 2017), pp. 1-12 (2017).

Simonyan et al., "Very Deep Convolutional Networks for Large-Scale Image Recognition," arXiv:1409.1556v6, pp. 1-14 (Apr. 10, 2015).

Zaitsev et al., "Motion Artefacts in MRI: a Complex Problem with Many Partial Solutions," J Magn Reson Imaging, vol. 42, No. 4, pp. 1-30 (Oct. 2015).

Andre et al., "Toward Quantifying the Prevalence, Severity, and Cost Associated with Patient Motion During Clinical MR Examinations," J Am Coll Radiol, vol. 12, pp. 689-695 (2015).

Budde et al., "Ultra-high resolution imaging of the human brain using acquisition-weighted imaging at 9.4 T," NeuroImage, vol. 86, pp. 592-598 (2014).

Maclaren et al., "Prospective Motion Correction in Brain Imaging: A Review," Magnetic Resonance in Medicine, vol. 69, pp. 621-636 (2013).

Schulz et al., "An embedded optical tracking system for motion-corrected magnetic resonance imaging at 7T," Magn Reson Mater Phy, vol. 25, pp. 443-453 (2012).

Maclaren et al., "Measurement and Correction of Microscopic Head Motion during Magnetic Resonance Imaging of the Brain," PLoS ONE, vol. 7, No. 11, pp. 1-9 (2012).

Ooi et al., "Prospective Real-Time Correction for Arbitrary Head Motion Using Active Markers," Magn Reson Med., vol. 62, No. 4, pp. 1-23 (Oct. 2009).

Qin et al., "Prospective Head Movement Correction for High Resolution MRI using an In-bore Optical Tracking System," Magn Reson Med., vol. 62, No. 4, pp. 1-22 (Oct. 2009).

Vertinsky et al., "Performance of PROPELLER relative to standard FSE T2-weighted imaging in pediatric brain MRI," Pediatr Radiol, vol. 39, pp. 1-10 (2009).

Sheikh et al., "Image Information and Visual Quality," IEEE Transactions on Image Processing, vol. 15, No. 2, pp. 430-444 (Feb. 2006).

Zhuo et al., "MR Artifacts, Safety, and Quality Control," RadioGraphics, vol. 26, pp. 275-297 (2006).

Zaitsev et al., "Magnetic resonance imaging of freely moving objects: Prospective real-time motion correction using an external optical motion tracking system," NeuroImage, vol. 31, pp. 1038-1050 (2006).

Wang et al., "Image Quality Assessment: From Error Visibility to Structural Similarity," IEEE Transactions on Image Processing, vol. 13, No. 4, pp. 1-14 (Apr. 2004).

Wang et al., "Mulit-Scale Structural Similarity for Image Quality Assessment," Proceedings of the 37th IEEE Asilomar Conference on Signals, Systems and Computers, pp. 1-5 (Nov. 9-12, 2003).

Smith, "Fast Robust Automated Brain Extraction," Human Brain Mapping, vol. 17, pp. 143-155 (2002).

Wang et al., "A Universal Image Quality Index," IEEE Signal Processing Letters, vol. XX, No. Y, pp. 1-4 (Mar. 2002).

Zhang et al., "Segmentation of Brain MR Images Through a Hidden Markov Random Field Model and the Expectation-Maximization Algorithm," IEEE Transactions on Medical Imaging, vol. 20, No. 1, pp. 45-57 (Jan. 2001).

Pipe, "Motion Correction With PROPELLIER MRI: Application to Head Motion and Free-Breathing Cardiac Imaging," Magnetic Resonance in Medicine, vol. 42, pp. 1-7 (1999).

Perlin, "An Image Synthesizer," SIGGRAPH '85, vol. 19, No. 3, pp. 1-10 (Jul. 22-26, 1985).

Commonly-Assigned, co-pending U.S. Appl. No. 17/139,426 for "Methods, Systems, and Computer Readable Media for Accelerating Diffusion Magnetic Resonance Imaging (MRI) Acquisition Via Slice-Interleaved Diffusion Encoding," (Unpublished, filed Dec. 31, 2020).

"Generative adversarial network," Wikipedia, pp. 1-10 (Dec. 7, 2019).

"Neural Network," Wikipedia, pp. 1-10 (Nov. 12, 2019).

Pelxelro, "Hitchhiker's Guide to Residual Networks (ResNet) in Keras," https://towardsdatascience.com/hitchhikers-guide-to-residual-networks-resnet-in-keras-385ec01ec8ff, pp. 1-8 (Apr. 8, 2019).

Kumar, "Autoencoder: Downsampling and Upsampling," OpenGenus, pp. 1-7 (Feb. 15, 2019).

Isola et al., "Image-to-Image Translation with Conditional Adversarial Networks," arXiv:1611.07004v3 (Nov. 26, 2018).

Zhu et al., "Unpaired Image-to-Image Translation using Cycle-Consisent Adversarial Networks," arXiv:1703.10593v6, pp. 1-18 (Nov. 15, 2018).

Non-Final Office Action for U.S. Appl. No. 17/139,426, (dated Feb. 3, 2022).

* cited by examiner

METHODS, SYSTEMS, AND COMPUTER READABLE MEDIA FOR USING A TRAINED ADVERSARIAL NETWORK FOR PERFORMING RETROSPECTIVE MAGNETIC RESONANCE IMAGING (MRI) ARTIFACT CORRECTION

PRIORITY CLAIM

This application claims the priority benefit of U.S. Provisional Patent Application Ser. No. 62/950,926, filed Dec. 19, 2019, the disclosure of which is incorporated herein by reference in its entirety.

GOVERNMENT INTEREST

This invention was made with government support under Grant Nos. EB006733 and MH110274 awarded by the National Institutes of Health. The government has certain rights in the invention.

TECHNICAL FIELD

The subject matter described herein relates to retrospective magnetic resonance imaging (MRI) artifact correction. More particularly, the subject matter described herein relates to using a trained adversarial network for performing retrospective MRI artifact correction.

BACKGROUND

Structural magnetic resonance imaging (MRI) is highly susceptible to motion related artifacts, which can be difficult to avoid, especially for pediatric subjects. Deep learning based retrospective MRI artifact correction can be employed to improve image quality. One example deep learning based system may require supervised training of a neural network using paired data, e.g., images of a subject with no artifacts and images of the same subject with artifacts. However, acquiring a large amount of paired data for supervised training is impractical since generating images displaying a wide range of artifacts is challenging.

Accordingly, in light of these difficulties, there exists a need for improved methods, systems, and computer readable media for using a trained adversarial network for performing retrospective MRI artifact correction.

SUMMARY

The subject matter described herein relates to methods, systems, and computer readable media for using a trained adversarial network for performing retrospective magnetic resonance imaging (MRI) artifact correction. An example method includes receiving, as input, an MRI image having at least one artifact; using a trained adversarial network for performing retrospective artifact correction on the MRI image, wherein the trained adversarial network is trained using unpaired artifact-free MRI images and artifact-containing MRI images; and outputting, by the trained adversarial network, a derivative MRI image related to the input, wherein the at least one artifact is corrected in the derivative MRI image.

An example system for performing retrospective MRI artifact correction includes at least one computing platform including at least one processor; and a trained adversarial network executable by the at least one processor for receiving, as input, an MRI image having at least one artifact; using a trained adversarial network for performing retrospective artifact correction on the MRI image, wherein the trained adversarial network is trained using unpaired artifact-free MRI images and artifact-containing MRI images; and outputting, by the trained adversarial network, a derivative MRI image related to the input, wherein the at least one artifact is corrected in the derivative MRI image.

The subject matter described herein can be implemented in software in combination with hardware and/or firmware. For example, the subject matter described herein can be implemented in software executed by a processor. In one exemplary implementation, the subject matter described herein can be implemented using a non-transitory computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

Various embodiments of the subject matter described herein will now be explained with reference to the accompanying drawings, wherein like reference numerals represent like parts, of which.

DETAILED DESCRIPTION

The subject matter described herein involves methods, systems, and computer readable media for using a trained adversarial network for performing retrospective magnetic resonance imaging (MRI) artifact correction. Reference will now be made in detail to various embodiments of the subject matter described herein, examples of which are illustrated in the accompanying drawings. Wherever possible, the same reference numbers will be used throughout the drawings to refer to the same or like parts.

In accordance with some aspects of the subject matter described herein, techniques, methods, or mechanisms are disclosed for using a trained adversarial network for performing retrospective MRI artifact correction. For example, an example trained adversarial network may involve one or more computer algorithms trained to transform or translate an artifact-containing MRI image (e.g., an MRI image containing image imperfections such as noise, streaking, and ghosting) to an artifact-free MRI image (e.g., an MRI image with the image imperfections removed and/or corrected). In this example, the trained adversarial network may be trained using one or more unsupervised training techniques, e.g., using a set of artifact-containing MRI images and a set of artifact-free MRI images that are not matched or paired (e.g., one image set may be taken from subjects that are different than the other image set) to train one or more aspects (e.g., a generator and a discriminator) of the adversarial network.

In accordance with some aspects of the subject matter described herein, techniques, methods, or mechanisms are disclosed for training content-swapping and/or content disentanglement aspects of an adversarial network usable for performing retrospective MRI artifact correction. For example, an adversarial network in accordance with various aspects herein may be trained to disentangle (e.g., separate) and encode MRI content and MRI artifact information from one or more sources (e.g., MRI images) and to generate images using encoded MRI content information and encoded MRI artifact information from the one or more sources.

In some embodiments, an adversarial network in accordance with various aspects herein may be trained using a first autoencoder for translating images of a first image domain to a second image domain (e.g., an artifact-containing MRI image to an artifact-free MRI image) and a second autoencoder for translating images of the second image domain to the first image domain (e.g., an artifact-free MRI image to an artifact-containing MRI image). In this example, each autoencoder may include an artifact encoder for encoding artifact information associated with a first image of one image domain and a content encoder for encoding content information associated with that first image. Continuing with this example, each autoencoder may include a decoder for translating and/or decoding encoded content information and encoded artifact information into a derivative MRI image. In some embodiments, a decoder may generate an artificial (but realistic) MRI image usable for training purposes based on encoded content information and encoded artifact information from different images and/or image domains.

Advantageously, in accordance with some aspects of the subject matter described herein, by using unsupervised training techniques and/or unpaired image sets, an adversarial network can be trained efficiently to identify and remove artifacts with remarkable efficacy from artifact-containing images to recover or generate artifact-free counterparts, e.g., high-quality corrected images. Moreover, since a trained adversarial network described herein can be trained using one or more unsupervised training techniques, significant time and resources may be conserved since paired image sets (e.g., matching images with and without artifacts) are not needed and, as such, resources (e.g., time and effort) spent collecting and/or artificially generated such pairs are not required. Further, by using unsupervised training techniques, an adversarial network can be trained without explicitly specifying artifacts or their nature. As such, the trained adversarial network may effectively remove artifacts or imperfections (e.g., noise, streaking, and ghosting) from MRI images without explicit generating them for training purposes, unlike what supervised training of the adversarial network would require.

Figure 1:
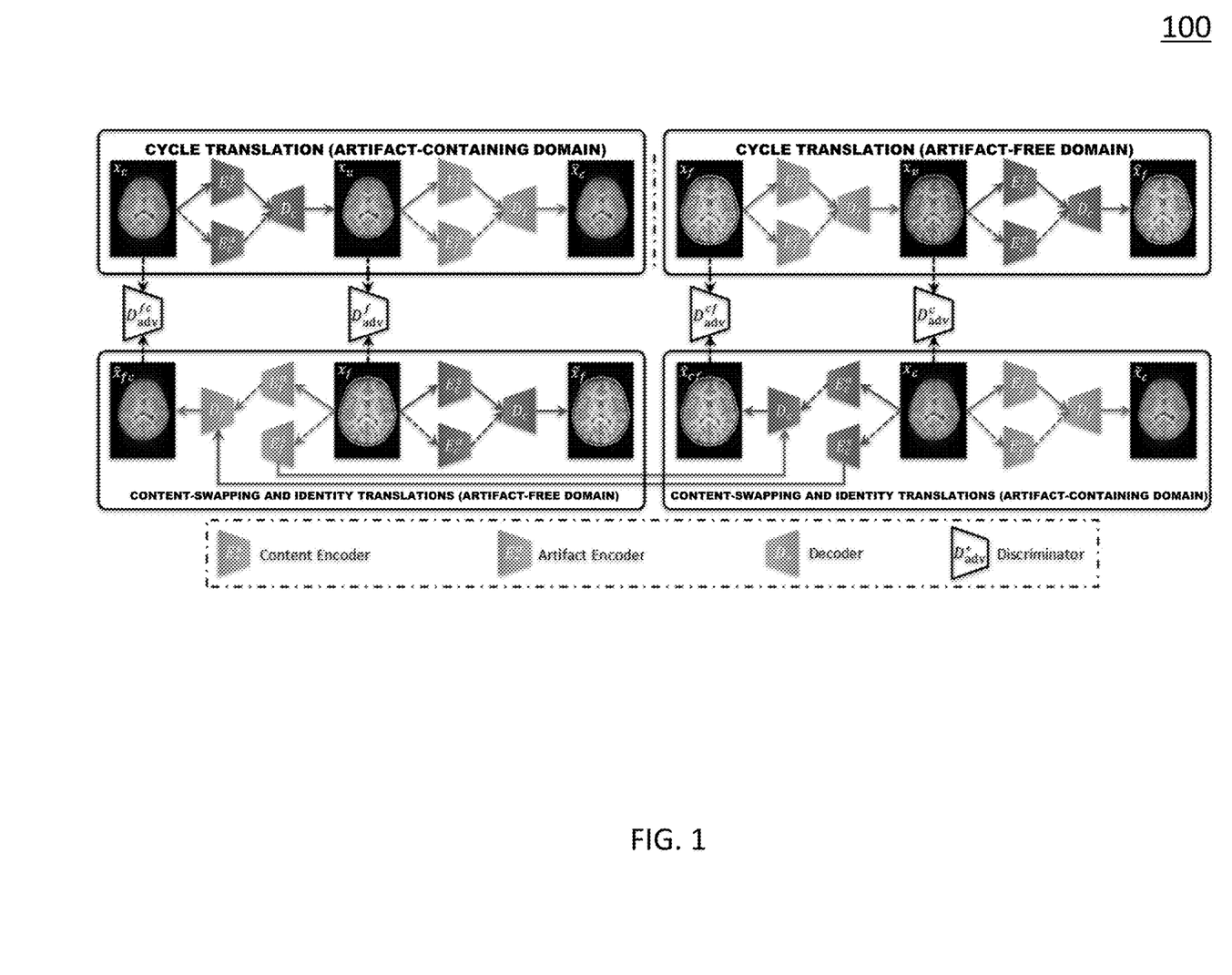
FIG. 1 is a diagram illustrating an example disentangled unsupervised cycle-consistent adversarial network (DUNCAN) for performing retrospective magnetic resonance imaging (MRI) artifact correction.

FIG. 1 is a diagram illustrating an example disentangled unsupervised cycle-consistent adversarial network (DUNCAN) 100 for performing retrospective MRI artifact correction. In some embodiments, DUNCAN 100 may represent one or more neural networks (e.g., algorithms) and/or related mechanisms for transforming or translating input (e.g., artifact-containing MRI images) into output (e.g., artifact-free MRI images) or vice versa.

In some embodiments, DUNCAN 100 may include or utilize one or more generative adversarial networks (GANs). In this example, each GAN may represent a type of machine learning system that utilizes a generator (e.g., one or more algorithms or neural networks) to transform or translate input to output and a discriminator (e.g., one or more algorithms or neural networks) to determine whether the generated output is real or synthesized. Continuing with this example, initial training data may involve two image domains, e.g., MRI images with artifacts and MRI images without artifacts. Using the training data and backpropagation involving output from the generator, the discriminator can learn to better identify synthetic MRI images from real MRI images. Similarly, using the training data and backpropagation involving output from the discriminator, the generator can learn to generate or synthesize more realistic MRI images. In some embodiments, a GAN may be trained by training the generator and the discriminator against each other until a predetermined condition is reached (e.g., a particular error rate for the discriminator is reached or a significant number of synthetic MRI images generated by the generator fool the discriminator). In some embodiments, a generator may include a convolutional neural network and a discriminator may include a convolutional neural network.

In some embodiments, training data may include sets of artifact-containing MRI images (e.g., a first image domain) and artifact-free MRI images (e.g., a second image domain). In such embodiments, these sets of MRI images may be unpaired and may be of different subjects (e.g., different brains). In some embodiments, MRI images usable for training may include T1-weighted MRI volumes and/or T2-weighted MRI volumes of pediatric subjects from birth to age six. For example, 20 artifact-free volumes and 20 artifact-containing volumes may be used for training an adversarial network or portion thereof and 5 artifact-containing volumes may be selected for testing. In this example, 1620, 1600, and 425 axial slices may be extracted, respectively, from the 20 artifact-free, 20 artifact-containing and 5 artifact-containing T1-weighted volumes and 1520, 1550 and 425 axial slices may be extracted, respectively, from the 20 artifact-free, 20 artifact-containing and 5 artifact-containing T2-weighted volumes.

In some embodiments, DUNCAN 100 may be trained for cycle consistency. For example, DUNCAN 100 may be trained such that a first autoencoder receives an MRI image as input and produces a derivative MRI image as output and that a second autoencoder receives the derivative MRI image and produces the original MRI image as output.

In some embodiments, when learning artifact-containing and artifact-free domains from training data, two autoencoders (similar to CycleGAN architecture discussed in [3]) may be used to learn a cycle translation (e.g., a disentangled cycle translation (DCT)) that translates forward and backward the images in the two domains. During training, two discriminators may be used to distinguish between translated (e.g., synthetic) and real images in each domain, e.g., each discriminator may be similar to patch-GAN discriminators discussed in [4]). In some embodiments, each auto-encoder may include two encoders (e.g., a content encoder and an artifact encoder) to disentangle content and artifact information. In some embodiments where two encoders are used for disentanglement of content and artifact, a content-swapping mechanism may be used where one or more translated images in each domain is generated using content information of the opposite domain. In some embodiments, training of DUNCAN 100 may enforce that when the input image is artifact-free, the output is unaltered with no removal of image details.

Referring to FIG. 1, DUNCAN 100 may be trained using cycle translations, e.g., an artifact-containing domain (ACD) cycle translation and an artifact-free domain (AFD) cycle translation. The ACD cycle translation may represent the process of translating an artifact-containing MRI image to an artifact-free MRI image then back to the artifact-containing MRI image. The ACD cycle translation may involve using a 'correcting' autoencoder including a content encoder and an artifact encoder for encoding respective portions of the artifact-containing MRI image and a decoder for translating the encoded portions into the artifact-free MRI image. The ACD cycle translation may further involve using a 'corrupting' autoencoder including a content encoder and an artifact encoder for encoding respective portions of the artifact-free MRI image and a decoder for translating the encoded portions back into the artifact-containing MRI image.

The AFD cycle translation may represent the process of translating an artifact-free MRI image to an artifact-containing MRI image then back to the artifact-free MRI image. The AFD cycle translation may involve using the 'corrupting' autoencoder for encoding respective portions of the artifact-free MRI image and a decoder for translating the encoded portions into the artifact-containing MRI image. The AFD cycle translation may further involve using the 'correcting' autoencoder for encoding respective portions of the artifact-containing MRI image and a decoder for translating the encoded portions back into the artifact-free MRI image.

In some embodiments, training of DUNCAN 100 may include utilizing identity translations and/or other learning mechanisms. For example, an AFD identity translation mechanism may involve a process of training so that an artifact-free MRI image is not altered (e.g., by removing non-existent artifacts) when inputted into a 'correcting' autoencoder, and an ACD identity translation mechanism may involve a process of training so that an artifact-containing MRI image is not altered (e.g., by adding additional artifacts) when inputted into a 'corrupting' autoencoder.

In some embodiments, training of DUNCAN 100 may include utilizing content-swapping for generating new training data and/or other learning mechanisms. For example, a content-swapping mechanism may involve generating or synthesizing a realistic MRI image by inputting, into a decoder of a 'correcting' autoencoder, encoded content information derived from a real artifact-free MRI image and encoded artifact information derived from a real artifact-containing MRI image. In another example, a content-swapping mechanism may involve generating or synthesizing a realistic MRI image by inputting, into a decoder of a 'corrupting' autoencoder, encoded content information derived from a real artifact-containing MRI image and encoded artifact information derived from a real artifact-free MRI image.

In some embodiments, training of DUNCAN 100 may include training discriminators using content-swapped generated MRI images and real MRI images and/or training discriminators using non-content-swapped generated MRI images and real MRI images. For example, a discriminator may receive a real artifact-containing MRI image and a synthesized artifact-containing MRI image based on encoded data portion from two different images. In this example, by training discriminators using these additional MRI images, the discriminators can potentially improve its accuracy in identifying synthesized MRI images, which in turn can potentially improve the autoencoder ability to synthesize more realistic MRI images.

In some embodiments, training of DUNCAN 100 or various aspects thereof may involve using loss functions to enforce or maintain quality and consistency. For example, a pixel-wise consistency loss function may be used for enforcing identity translation mapping, two least-squares loss functions may be used for adversarial learning (e.g., when comparing output to real counterparts), or a multi-scale content consistency loss function based on pixel, low-level content features, and high-level content features between images may be used.

In some embodiments, to ensure that the image quality of an input image is similar to the translated image, a pixel-wise image quality consistency (IQC) loss function may aid or encourage auto-encoders in the translation mappings $M_{f \to c}$ and $M_{c \to f}$ to perform as identity translation mappings $M_{c \to c}$: $I_c \to I_c$ and $M_{f \to f}$: $I_f \to I_f$ when respectively given artifact-corrupted and artifact-free images. The IQC loss function may aid or encourage an artifact-free image generator to not remove image details when given a good quality image. Similarly, the IQC loss function may aid or encourage an artifact-corrupted image generator to not introduce any additional artifacts when given an artifact-corrupted image.

Figure 6:
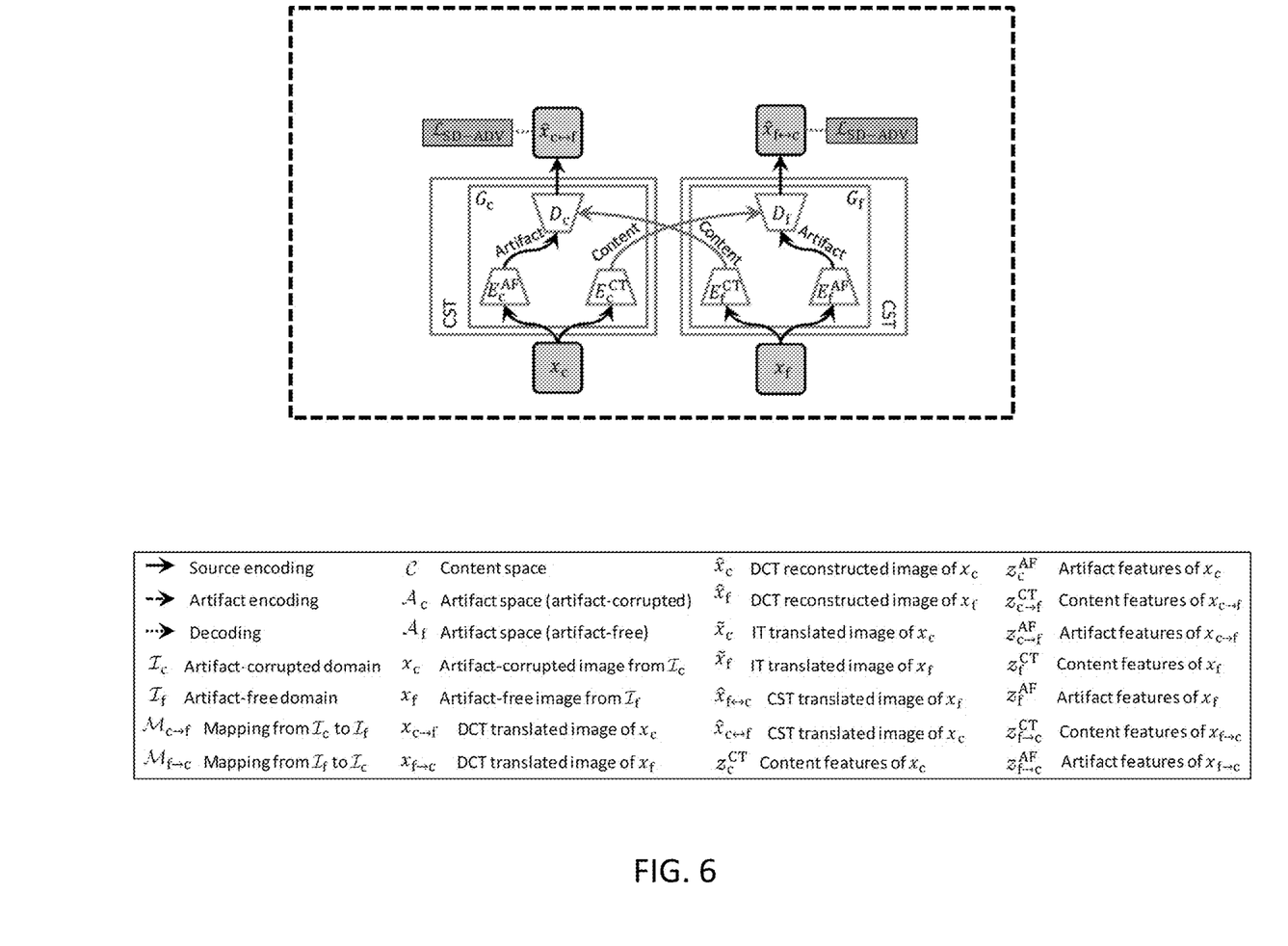
FIG. 6 illustrates example content swapping translation (CST) in artifact-corrupted and artifact-free domains.
Figure 7:
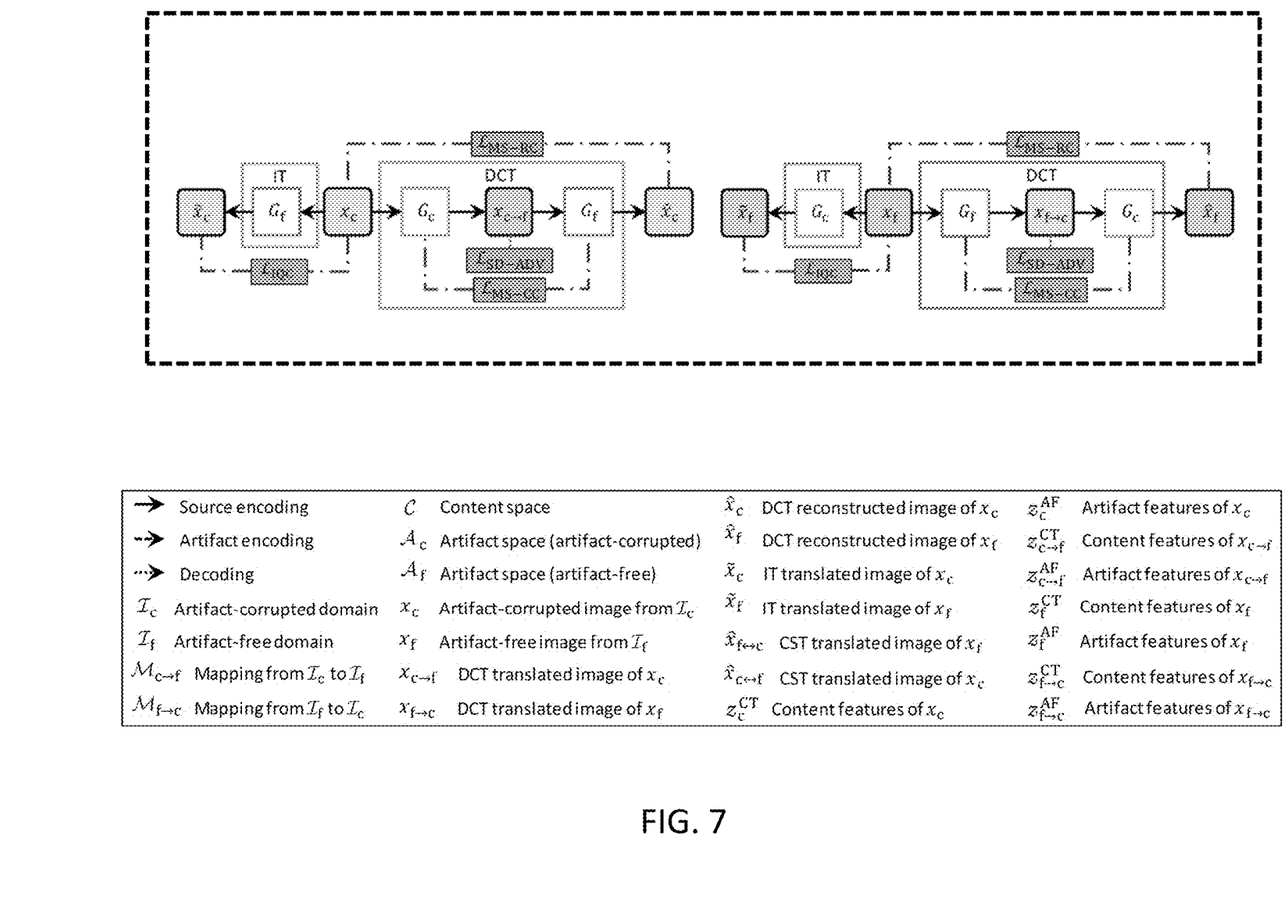
FIG. 7 illustrates example disentangled cycle translation (DCT) and identity translation (IT) in artifact-corrupted and artifact-free domains.

In some embodiments, consistency loss functions and adversarial loss functions may be used for facilitating model training, as illustrated in FIGS. 6 and 7.

In some embodiments, three consistency loss functions may be used facilitating model training. For example, a multi-scale content consistency (MS-CC) loss function $L_{MS\text{-}CC}$ may measure content consistency between the input and output of the forward translation of each DCT (e.g., $M_{c \to f}$ in $M_{c \to f \to c}$ and $M_{f \to c}$ in $M_{f \to c \to f}$), a multi-scale reconstruction consistency (MS-RC) loss function $L_{MS\text{-}RC}$ may compute the reconstruction consistency between an image and its reconstructed counterpart in the same domain, and an IQC loss function $L_{IQC}$ may compute the image quality consistency between an image and its identity translated counterpart in the same domain.

In some embodiments, an MS-CC loss function may measure low-level and high-level content feature differences and is formulated as $$\mathcal{L}_{MS\text{-}CC} = \Sigma_i [\mathbb{E}_{x_c \sim I_c} \|\phi_c^i(x_c) - \phi_c^i(x_{c \to f})\|_1 + \mathbb{E}_{x_f \sim I_f} \|\phi_f^i(x_f) - \phi_c^i(x_{f \to c})\|_1], \quad (1)$$

where $x_c$ and $x_f$ denote the artifact-corrupted and artifact-free images, respectively, and $x_{c \to f} = D_c(z_f^{CT}, z_f^{AF})$ and $x_{f \to c} = D_f(z_f^{CT}, z_f^{AF})$ denote the corresponding artifact-free and artifact-corrupted images generated by the decoders, respectively, $\phi_c^i(\cdot)$ and $\phi_f^i(\cdot)$ denote the outputs of the i-th residual block of the content encoders $E_c^{CT}$ and $E_f^{CT}$, respectively. $z_c^{CT} = E_c^{CT}(x_c) \in C$ and $z_f^{CT} = E_f^{CT}(x_f) \in C$ denote the content information extracted respectively from $x_c$ and $x_f$, whereas $z_c^{AF}=E_c^{AF}(x_c) \in A_c$ and $z_f^{AF}=E_f^{AF}(x_f) \in A_f$ denote the artifact information extracted respectively from $x_c$ and $x_f$.

In some embodiments, an MS-CC loss function may be computed by combining three reconstruction consistency loss functions: a pixel reconstruction consistency (PRC) loss function $L_{PRC}$, an edge reconstruction consistency (ERC) loss function $L_{ERC}$, and a structure reconstruction consistency (SRC) loss function $L_{SRC}$, as defined below:

$$\mathcal{L}_{MS\text{-}RC}=\mathcal{L}_{PRC}+\mathcal{L}_{ERC}+\mathcal{L}_{SRC}, \tag{2}$$

$$\mathcal{L}_{PRC}=\mathbb{E}_{x_c \sim I_c}\|x_c-\hat{x}_c\|_1+\mathbb{E}_{x_f \sim I_f}\|x_f-\hat{x}_f\|_1, \tag{3}$$

$$\mathcal{L}_{ERC}=\mathbb{E}_{x_c \sim I_c}\|\psi_L(x_c)-\psi_L(\hat{x}_c)\|_1+\mathbb{E}_{x_f \sim I_f}\|\psi_L(x_f)-\psi_L(\hat{x}_f)\|_1, \tag{4}$$

$$\mathcal{L}_{SRC}=\mathbb{E}_{x_c \sim I_c}\|\psi_H(x_c)-\psi_H(\hat{x}_c)\|_1+\mathbb{E}_{x_f \sim I_f}\|\psi_H(x_f)-\psi_H(\hat{x}_f)\|_1, \tag{5}$$

where $\hat{x}_c=D_f(E_f^{CT}(x_{c \to f}), E_f^{AF}(x_{c \to f}))$ and $\hat{x}_f=D_c(E_c^{CT}(x_{f \to c}), E_c^{AF}(x_{f \to c}))$ are, respectively, the reconstructed images in the artifact-corrupted and artifact-free domains, and $\psi_L(\cdot)$ and $\psi_H(\cdot)$ are, respectively, the low-level structural information that reflects edges and high-level semantic information that reflects contents measured by a pre-trained network.

In some embodiments, an IQC loss function may be used for preserving image quality after translation when no alteration is expected. In such embodiments, the IQC loss function may measure the pixel-wise difference between the input and identity mapped images as $$\mathcal{L}_{IQC}=\mathbb{E}_{x_c \sim I_c}\|x_c-\tilde{x}_c\|_1+\mathbb{E}_{x_f \sim I_f}\|x_f-\tilde{x}_f\|_1, \tag{6}$$

Where $\tilde{x}_c=D_f(E_f^{CT}(x_c), E_f^{AF}(x_c))$ and $\tilde{x}_f=D_c(E_c^{CT}(x_f), E_c^{AF}(x_f))$ are the identity mapped images of $x_c$ and $x_f$, respectively.

In some embodiments, a single-domain adversarial (SD-ADV) loss function and a cross-domain adversarial (CD-ADV) loss function may be used to enhance the judgment accuracy of the discriminators. In some embodiments, all adversarial loss functions are designed with the mean square error function.

In some embodiments, an SD-ADV loss function may be calculated in a specific domain, e.g., $I_c$ or $I_f$, as $$\mathcal{L}_{SD\text{-}ADV}=\tfrac{1}{2}\mathbb{E}_{x_c \sim I_c}(D_c^{ADV}(x_c)-I)^2+\tfrac{1}{2}\mathbb{E}_{x_f \sim I_f}(D_c^{ADV}(x_{f \to c}))^2+\tfrac{1}{2}\mathbb{E}_{x_f \sim I_f}(D_f^{ADV}(x_f)-I)^2+\tfrac{1}{2}\mathbb{E}_{x_c \sim I_c}(D_f^{ADV}(x_{c \to f}))^2 \tag{7}$$

where $D_c^{ADV}$ and $D_f^{ADV}$ are the discriminators used to distinguish between real and fake images respectively in domains $I_c$ and $I_f$. I is a matrix of ones with size $N_1 \times N_2$ matching the output of the discriminator.

In some embodiments, a CD-ADV loss function may be defined as $$\mathcal{L}_{CD\text{-}ADV}=\tfrac{1}{2}\mathbb{E}_{x_c \sim I_c}(D_{f \leftrightarrow c}^{ADV}(x_c)-I)^2+\tfrac{1}{2}\mathbb{E}_{x_f \sim I_f x_c \sim I_c}(D_{f \leftrightarrow c}^{ADV}(\hat{x}_{f \leftrightarrow c}))^2+\tfrac{1}{2}\mathbb{E}_{x_f \sim I_f}(D_{c \leftrightarrow f}^{ADV}(x_f)-I)^2+\tfrac{1}{2}\mathbb{E}_{x_c \sim I_c x_f \sim I_f}(D_{c \leftrightarrow f}^{ADV}(\hat{x}_{c \leftrightarrow f}))^2 \tag{8}$$

where $\hat{x}_{c \leftrightarrow f}=D_c(z_c^{CT}, z_c^{AF})$ and $\hat{x}_{f \leftrightarrow c}=D_f(z_f^{CT}, z_f^{AF})$ are the images reconstructed by cross-domain content information (e.g., $z_f^{CT}$ or $z_c^{CT}$) and current-domain artifact information (e.g., $z_c^{AF}$ or $z_f^{AF}$).

In some embodiments, a total loss function of DUNCAN 100 may be $$\mathcal{L}_{total}=\mathcal{L}_{SD\text{-}ADV}+\mathcal{L}_{CD\text{-}ADV}+\lambda_{MS\text{-}CC}\mathcal{L}_{MS\text{-}CC}+\lambda_{PRC}\mathcal{L}_{PRC}+\lambda_{ERC}\mathcal{L}_{ERC}+\lambda_{SRC}\mathcal{L}_{SRC}+\lambda_{IQC}\mathcal{L}_{IQC} \tag{9}$$

where $\lambda_{MS\text{-}CC}$, $\lambda_{PRC}$, $\lambda_{ERC}$, $\lambda_{SRC}$, and $\lambda_{IQC}$ are the loss weights used for controlling the contributions of the terms in term in Equation (9).

In some embodiments, an implementation of DUNCAN 100 may use a deep learning Python-based application programming interface (API) named Keras and a TensorFlow 2.0 backend and may be based on a computer (e.g., a physical machine or a virtual machine) with a central processing unit (CPU) (e.g., an Intel i7-8700K processor) and a graphics processing unit (GPU) (e.g., an NVIDIA GeForce GTX 1080Ti 11 GB RAM processor).

In some embodiments, an implementation of DUNCAN 100 may utilize an Adam optimizer with an $1 \times 10^{-4}$ learning rate for minimizing the loss function. In this DUNCAN implementation, for in vivo T1-weighted and T2-weighted datasets, $\lambda_{MS\text{-}CC}=5$, $\lambda_{PCC}=10$, $\lambda_{ERC}=5$, $\lambda_{SRC}=5$, and $\lambda_{IQC}=1$ may be example weight values for MS-CC, PRC, ERC, SRC, and IQC losses, respectively. In this DUNCAN implementation, for in silico T1-weighted and T2-weighted datasets, $\lambda_{MS\text{-}SCC}=10$, $\lambda_{PCC}=20$, $\lambda_{ERC}=10$, $\lambda_{SRC}=10$, and $\lambda_{IQC}=5$ may be example weight values for MS-CC, PRC, ERC, SRC, and IQC losses, respectively. In this DUNCAN implementation, for in vivo and in silico datasets, every three adjacent slices in each volume may be inserted into RGB channels of a color image, which may then be normalized to have a range between −1 and 1 and cropped to 208×256 from the geometric center. During training of this Duncan implementation, one artifact-corrupted image from an artifact-corrupted dataset and one artifact-free image from an artifact-free dataset may be randomly selected each time as inputs.

It will be appreciated that FIG. 1 is for illustrative purposes and that various entities, their locations, and/or their functions may be changed, altered, added, or removed. For example, some entities and/or functions may be combined into a single entity. In another example, an entity and/or function may be located at or implemented by two or more entities.

Figure 2:
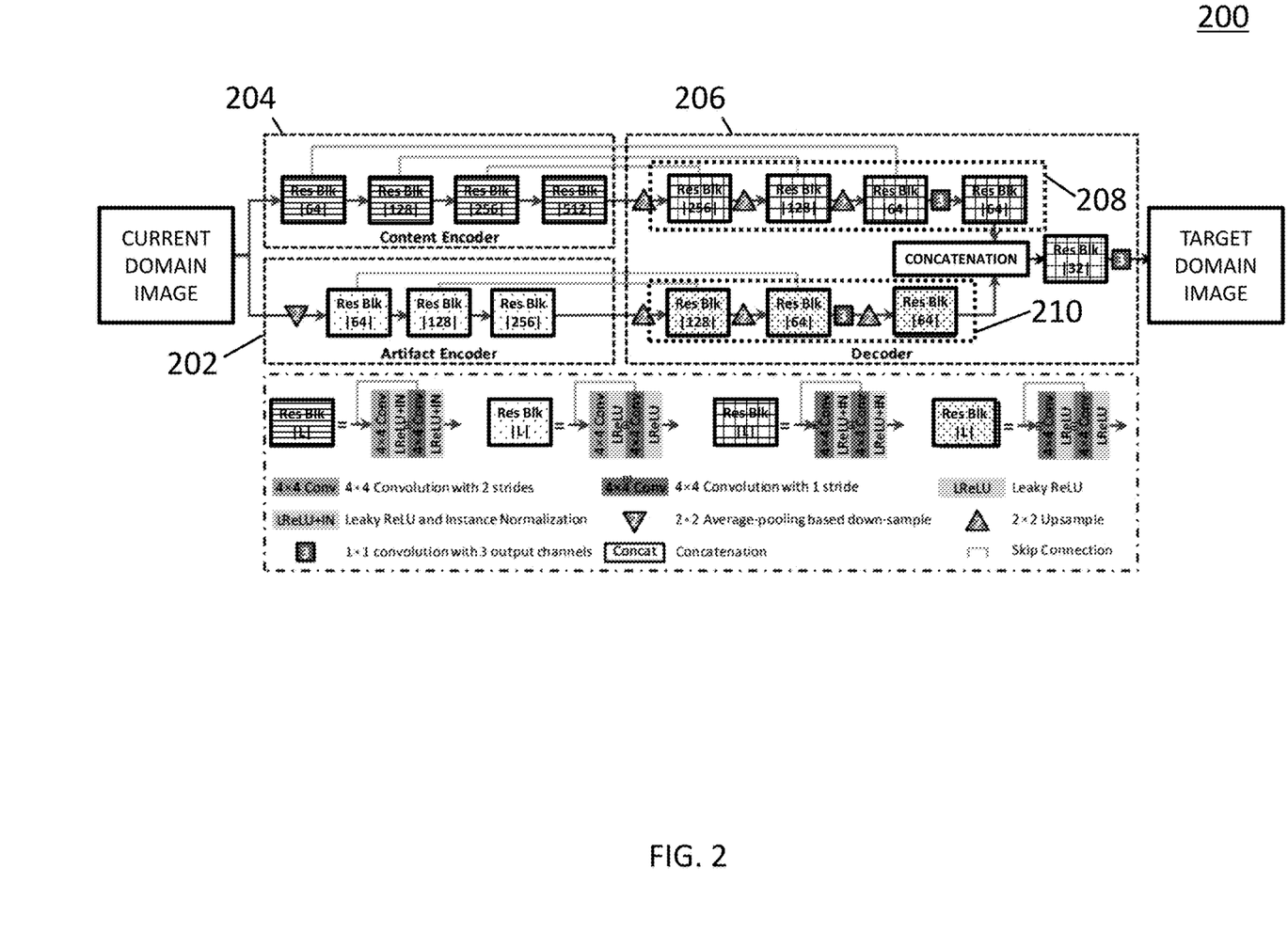
FIG. 2 is a diagram illustrating an example autoencoder usable by a DUNCAN.

FIG. 2 is a diagram illustrating an example autoencoder 200 usable by DUNCAN 100. In some embodiments, autoencoder 200 may be usable for translating an image from a current image domain to a target image domain (e.g., translating from an artifact-containing MRI image to an artifact-free MRI image.

Referring to FIG. 2, autoencoder 200 may include an artifact encoder 202 for encoding artifact information from input images, a content encoder 204 for encoding content information (e.g., non-artifact information) from input images, and a decoder 206 for translating and/or decoding encoded artifact information and encoded content information into an output image.

In some embodiments, artifact encoder 202, content encoder 204, and decoder 206 may each use one or more residual networks (e.g., neural networks that includes residual blocks). In some embodiments, each residual block may represent a set of algorithms for converting or translating input into output. Residual block may also have a connection that allow some output to skip or jump some blocks or related processing steps and to be used by other (e.g., deeper) residual blocks.

Artifact encoder 202 may include three residual blocks of different sizes. Each of these three residual blocks may include a series of algorithms usable for processing, e.g., 4×4 convolution with two strides, a leaky rectified linear unit (ReLU), 4×4 convolution with one stride, and a leaky ReLU. Prior to being received and processed by a first residual block (res blk |64|), input may be down-sampled using a 2×2 average pooling technique. After processing by the first residual block, output from the first residual block is sent as input to a second residual block (res blk |128|) for processing and, after processing by the second residual block, output from the second residual block is sent as input to a third residual block (res blk |256|) for processing. Output from the third residual block is then sent to decoder 206 (e.g., a first residual block of (res blk |128|) of artifact decoder 210) as input.

Content encoder 204 may include four residual blocks of different sizes. Each of these four residual blocks may include a series of algorithms usable for processing, e.g., 4×4 convolution with two strides, a leaky ReLU and instance normalization, 4×4 convolution with one stride, and a leaky ReLU and instance normalization. Input may be received and processed by a first residual block (res blk |64|). After processing by the first residual block, output from the first residual block is sent as input to a second residual block (res blk |128|) for processing; and, after processing by the second residual block, output from the second residual block is sent as input to a third residual block (res blk |256|) for processing; and, after processing by the third residual block, output from the third residual block is sent as input to a fourth residual block (res blk |512|) for processing. Output from the fourth residual block is then sent to decoder 206 (e.g., a first residual block of (res blk |256|) of content decoder 208) as input.

Decoder 206 may include two sets of residual blocks, one set for content decoder 208 and another set for 'artifact decoder' 210. Content decoder 208 may utilize residual blocks for processing input from the content encoder and artifact decoder 210 may utilize residual blocks for processing input from the artifact encoder. Each residual block of content decoder 208 may include a series of algorithms usable for processing, e.g., 4×4 convolution with one stride, a leaky ReLU and instance normalization, 4×4 convolution with one stride, and a leaky ReLU and instance normalization. Prior to being received and processed by a first residual block (res blk |256|) of content decoder 208, input (e.g., encoded content information from content encoder 204) may be up-sampled using a 2×2 up-sampling technique, e.g., an unpooling or transpose convolution technique. In addition to the up-sampled data, the first residual block of content decoder 208 may also receive input from a corresponding residual block of content encoder 204. After processing by the first residual block of content decoder 208, output from the first residual block of content decoder 208 is further up-sampled and sent as input, along with input from a corresponding residual block of content encoder 204, to a second residual block (res blk |128|) of content decoder 208 for processing; and, after processing by the second residual block of content decoder 208, output from the second residual block of content decoder 208 is further up-sampled and sent as input, along with input from a corresponding residual block of content encoder 204, to a third residual block (res blk |64|) of content decoder 208 for processing. After processing by the third residual block of content decoder 208, output from the third residual block of content decoder 208 is processed using 1×1 convolution with three output channels. The output from the 1×1 convolution with three output channels is then sent as input to a fourth residual block (res blk |64|) of content decoder 208 for processing. Output from the fourth residual block of content decoder 208 is then used as input by a concatenation algorithm.

Each residual block of artifact decoder 210 may include a series of algorithms usable for processing, e.g., 4×4 convolution with one stride, a leaky ReLU, 4×4 convolution with one stride, and a leaky ReLU. Prior to being received and processed by a first residual block (res blk |128|) of artifact decoder 210, input (e.g., encoded artifact information from artifact encoder 202) may be up-sampled using a 2×2 up-sampling technique, e.g., an unpooling or transpose convolution technique. In addition to the up-sampled data, the first residual block of artifact decoder 210 may also receive input from a corresponding residual block of artifact encoder 202. After processing by the first residual block of artifact decoder 210, output from the first residual block of artifact decoder 210 is further up-sampled and sent as input, along with input from a corresponding residual block of content encoder 202, to a second residual block (res blk |64|) of artifact decoder 210 for processing. After processing by the second residual block of artifact decoder 210, output from the third residual block of artifact decoder 210 is processed using 1×1 convolution with three output channels. The output from the 1×1 convolution with three output channels is then up-sampled and sent as input to a third residual block (res blk |64|) of artifact decoder 210 for processing. Output from the third residual block of artifact decoder 210 is then used as input by a concatenation algorithm of decoder 206.

The concatenation algorithm of decoder 206 may combine outputs from content decoder 208 and artifact decoder 210. The combined output may then be processed by a residual block (res blk |32|) of decoder 206, where the residual block may include a series of algorithms usable for processing, e.g., 4×4 convolution with one stride, a leaky ReLU and instance normalization, 4×4 convolution with one stride, and a leaky ReLU and instance normalization. The output from this residual block may then be processed using 1×1 convolution with three output channels to output the translated image.

It will be appreciated that FIG. 2 is for illustrative purposes and that various entities (e.g., residual blocks or related mathematical functions), their locations, and/or their functions may be changed, altered, added, or removed. For example, some entities and/or functions may be combined into a single entity. In another example, an entity and/or function may be located at or implemented by two or more entities.

Figure 3:
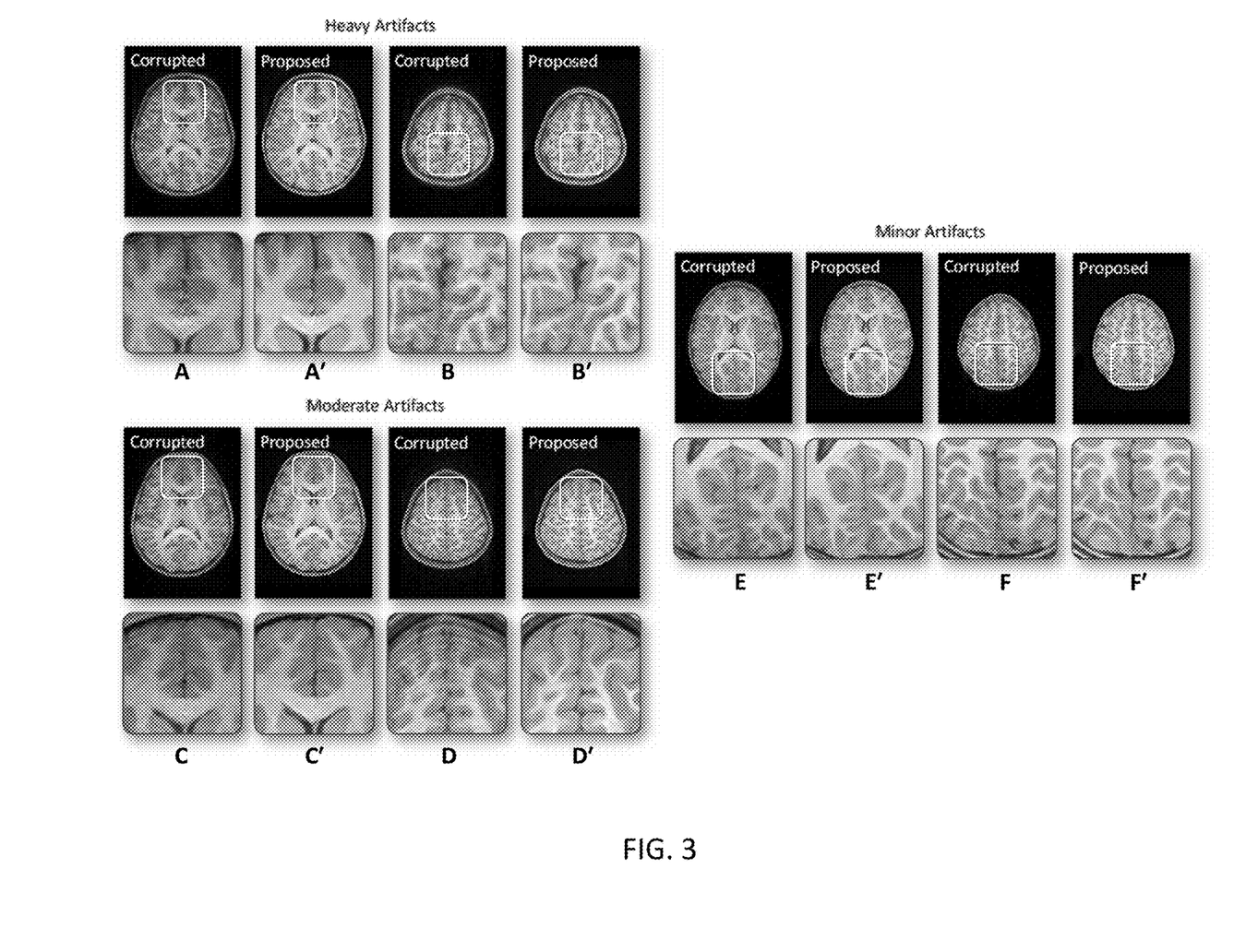
FIG. 3 shows example results for T1-weighted images after retrospective MRI artifact correction by a trained adversarial network.

FIG. 3 shows example results for T1-weighted images after retrospective MRI artifact correction by a trained adversarial network. In FIG. 3, two heavy artifact correction examples, two moderate artifact correction examples, and two minor artifact correction examples are provided. Each depicted correction example in FIG. 3 may include a corrupted MRI image and a corrected or proposed MRI image generated by a trained adversarial network, along with a zoomed-in portion of the corrupted MRI image (e.g., image 'A') and a zoomed-in portion of the proposed MRI image (e.g., image 'A'). It can be observed in FIG. 3 that artifacts are removed without significantly introducing new artifacts.

Figure 4:
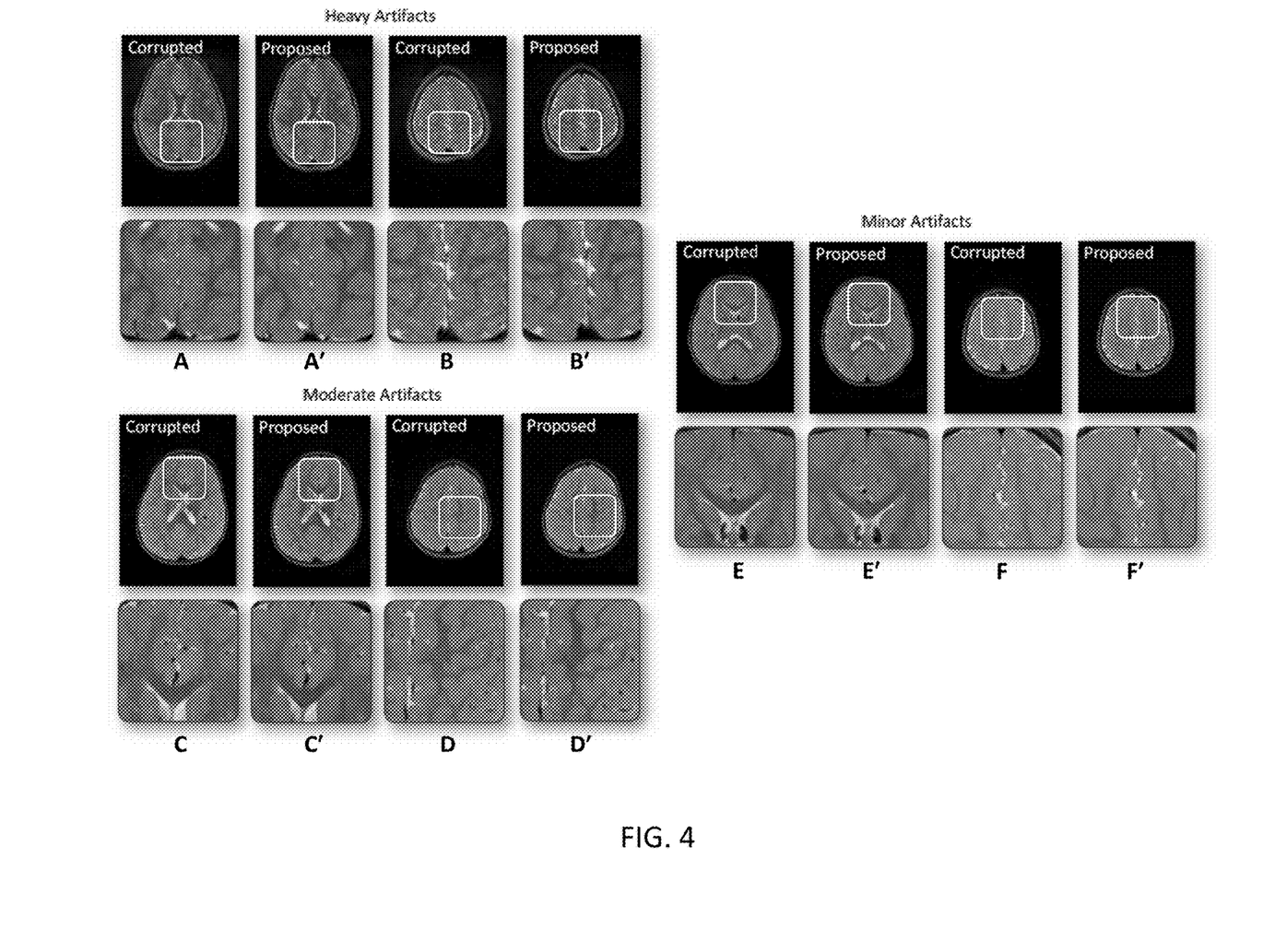
FIG. 4 shows example results for T2-weighted images after retrospective MRI artifact correction by a trained adversarial network.

FIG. 4 shows example results for T2-weighted images after retrospective MRI artifact correction by a trained adversarial network. In FIG. 4, two heavy artifact correction examples, two moderate artifact correction examples, and two minor artifact correction examples are provided. Each depicted correction example in FIG. 4 may include a corrupted MRI image and a corrected or proposed MRI image generated by a trained adversarial network, along with a zoomed-in portion of the corrupted MRI image (e.g., image 'A') and a zoomed-in portion of the proposed MRI image (e.g., image 'A'). It can be observed in FIG. 4 that artifacts are removed without significantly introducing new artifacts.

Figure 5:
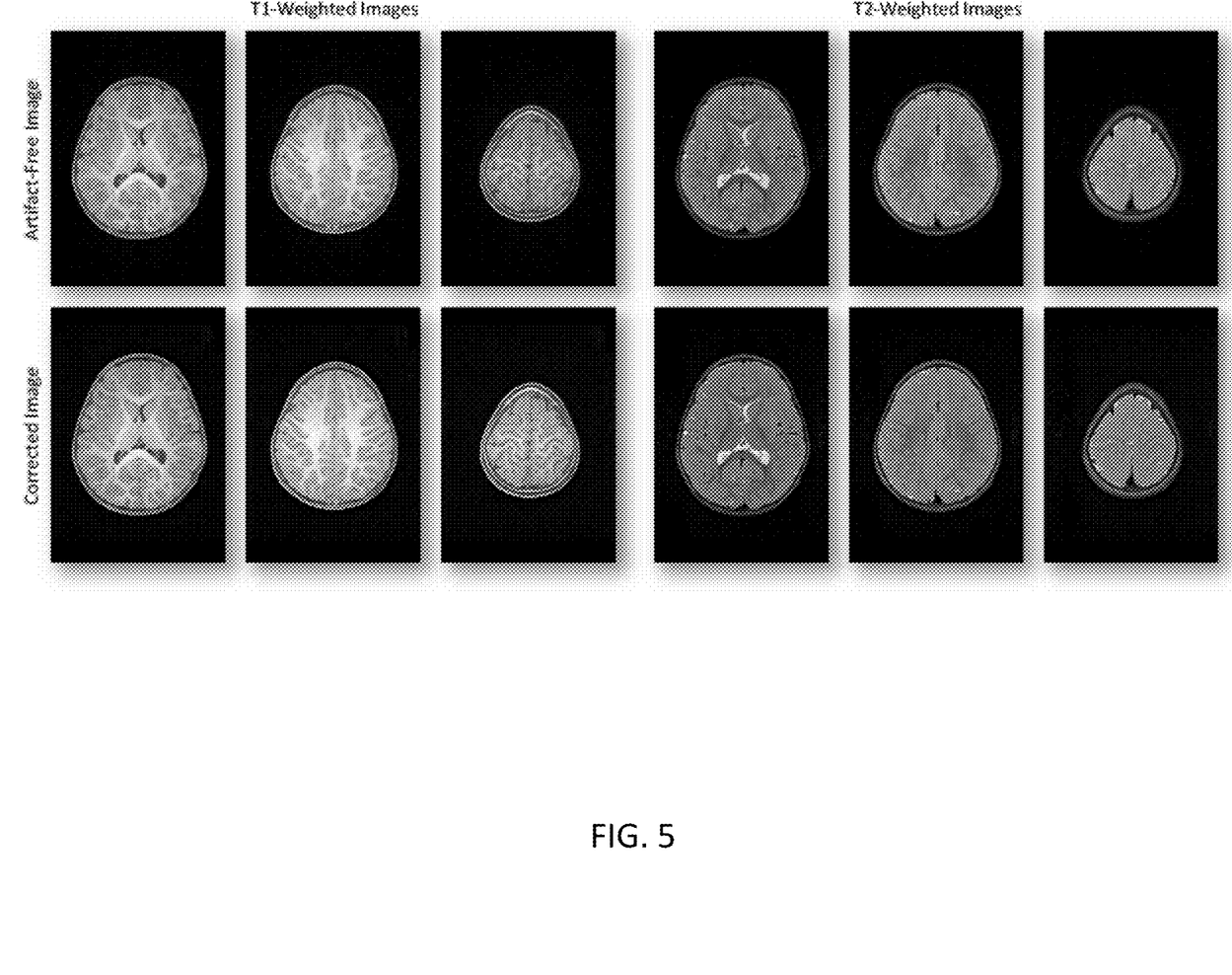
FIG. 5 shows example results for artifact-free images after retrospective MRI artifact correction by a trained adversarial network.

FIG. 5 shows example results for artifact-free images after retrospective MRI artifact correction by a trained adversarial network. In FIG. 5, three T1-weighted artifact correction examples and three T2-weighted correction examples are provided. Each depicted correction example in FIG. 5 may include an artifact-free MRI image and a corrected MRI image generated by a trained adversarial network. As shown, the corrected MRI image is not over-corrected since the trained adversarial network is trained to maintain image quality, e.g., enforcing that when the input image is artifact-free, the output is unaltered with no removal of image details.

FIG. 6 illustrates example content swapping translation (CST) in artifact-corrupted and artifact-free domains. As shown in FIG. 6, two auto-encoders $G_c$ and $G_f$ respectively generate artifact-free and artifact-corrupted images. Each auto-encoder may include a content encoder, $E_c^{CT}$ or $E_f^{CT}$ (e.g., content encoder 204), and an artifact encoder, $E_c^{AF}$ or $E_f^{AF}$ (e.g., artifact encoder 202), that respectively map an input image to the domain-invariant latent space C and the domain-specific latent space, $A_c$ or $A_f$, to respectively extract the content and artifact information of the image. Each auto-encoder may also include a decoder, $D_c$ or $D_f$ (e.g., decoder 206), that generates from the extracted features an image in the target domain of the auto-encoder. As depicted in FIG. 6, CST supports the idea that that when content information and artifact information are completely disentangled, swapping the domain-invariant content information between domain translations should not lead to changes in translation outcomes. For example, content information from $E_c^{CT}(x_c)$ in domain translation $M_{c \rightarrow f}$ may be replaced with content information from $E_f^{CT}(x_f)$ to construct content-swapped translated image $\hat{x}_{c \leftrightarrow f} \in I_f$ via decoder $D_c$. Similarly, content information from $E_f^{CT}(x_f)$ in domain translation $M_{f \rightarrow c}$ may be replaced with content information from $E_c^{CT}(x_c)$ to generate content-swapped translated image $\hat{x}_{f \leftrightarrow c} \in I_c$ via decoder $D_f$. The translated images $\hat{x}_{c \leftrightarrow f}$ and $\hat{x}_{f \leftrightarrow c}$, respectively, may be constrained by $x_f$ and $x_c$ via respective discriminators.

FIG. 7 illustrates example DCT and identity translation (IT) in artifact-corrupted and artifact-free domains. As shown in FIG. 7, DCT may involve an autoencoder (e.g., $G_c$) generating a DCT translated image (e.g., $x_{c \rightarrow f}$) and the DCT translated image being inputted into another autoencoder (e.g., $G_f$), where a MS-CC loss function is used for keeping content features consistent across domains. An SD-ADV loss function may be used for enhancing judgement accuracy of a discriminator that judges the DCT translated image. An MS-RC loss function may be used for maintaining reconstruction consistency between an image and its reconstructed counterpart in the same domain. IT may involve an autoencoder (e.g., $G_c$) receiving as an input an MRI image (e.g., $x_f$) and outputs an MRI image (e.g., $\tilde{x}_f$) that is not altered, where an IQC loss function is used for maintaining image quality when no alteration is expected. Forward translation mappings may be constrained with IT mappings. For example, when translation mappings $M_{c \rightarrow f}$ and $M_{f \rightarrow c}$ are applied to $\tilde{x}_f \in I_f$ and $x_c$, respectively, the mappings are constrained to result in identity reconstructions $\tilde{x}_f \in I_f$ and $\tilde{x}_c \in I_c$. A set of consistency loss functions may be used to ensure that the identity translated images are consistent with the corresponding input images.

Figure 8:
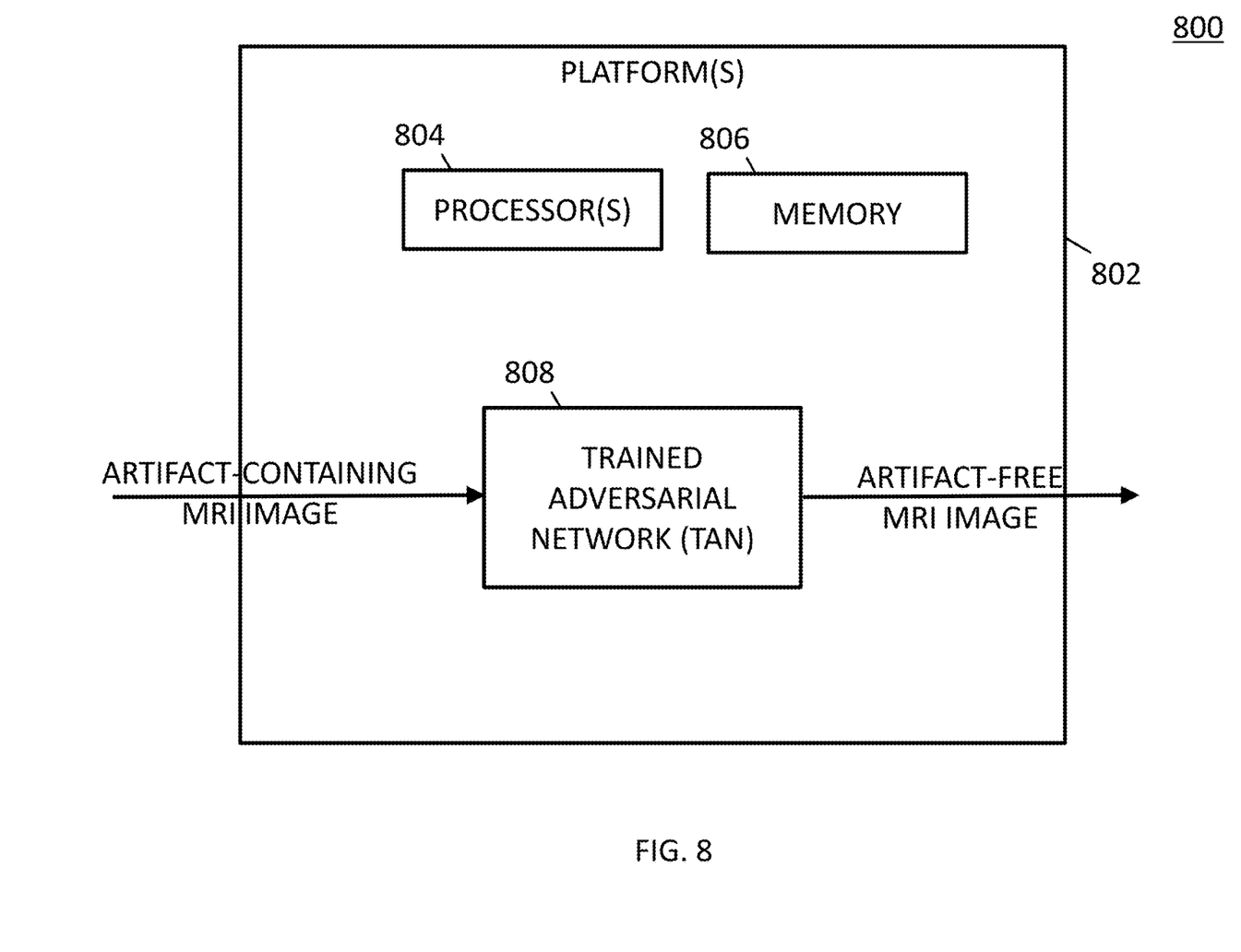
FIG. 8 is a block diagram of an example system for performing retrospective MRI artifact correction.

FIG. 8 is a block diagram of an example system 800 for performing retrospective MRI artifact correction. In FIG. 8, system 800 may include one or more computing platform(s) 802 having one or more processor(s) 804 and memory 806. A trained adversarial network (TAN) 808 may reside on computing platform(s) 802 and be executable by processor(s) 804. TAN 808 may receive an artifact-containing MRI image as input and may generate an artifact-free MRI image (e.g., an artifact-free version or derivate of the input artifact-containing MRI image) as output. In some embodiments, TAN 808 may represent DUNCAN 100 trained using one or more aspects described herein.

In some embodiments, computing platform(s) 102 with TAN 808 may be located in a cloud network. In such embodiments, cloud-based TAN 808 may receive an artifact-containing MRI image from an on-premise network of a user, may perform retrospective MRI artifact correction, and may provide, as output, an artifact-free MRI image.

In some embodiments, computing platform(s) 102 with TAN 808 may be located in an on-premise or local network of a user. In such embodiments, TAN 808 may receive an artifact-containing MRI image, may perform retrospective MRI artifact correction, and may provide, as output, an artifact-free MRI image.

It will be appreciated that FIG. 8 is for illustrative purposes and that various entities, their locations, and/or their functions may be changed, altered, added, or removed. For example, some entities and/or functions may be combined into a single entity. In another example, an entity and/or function may be located at or implemented by two or more entities.

Figure 9:
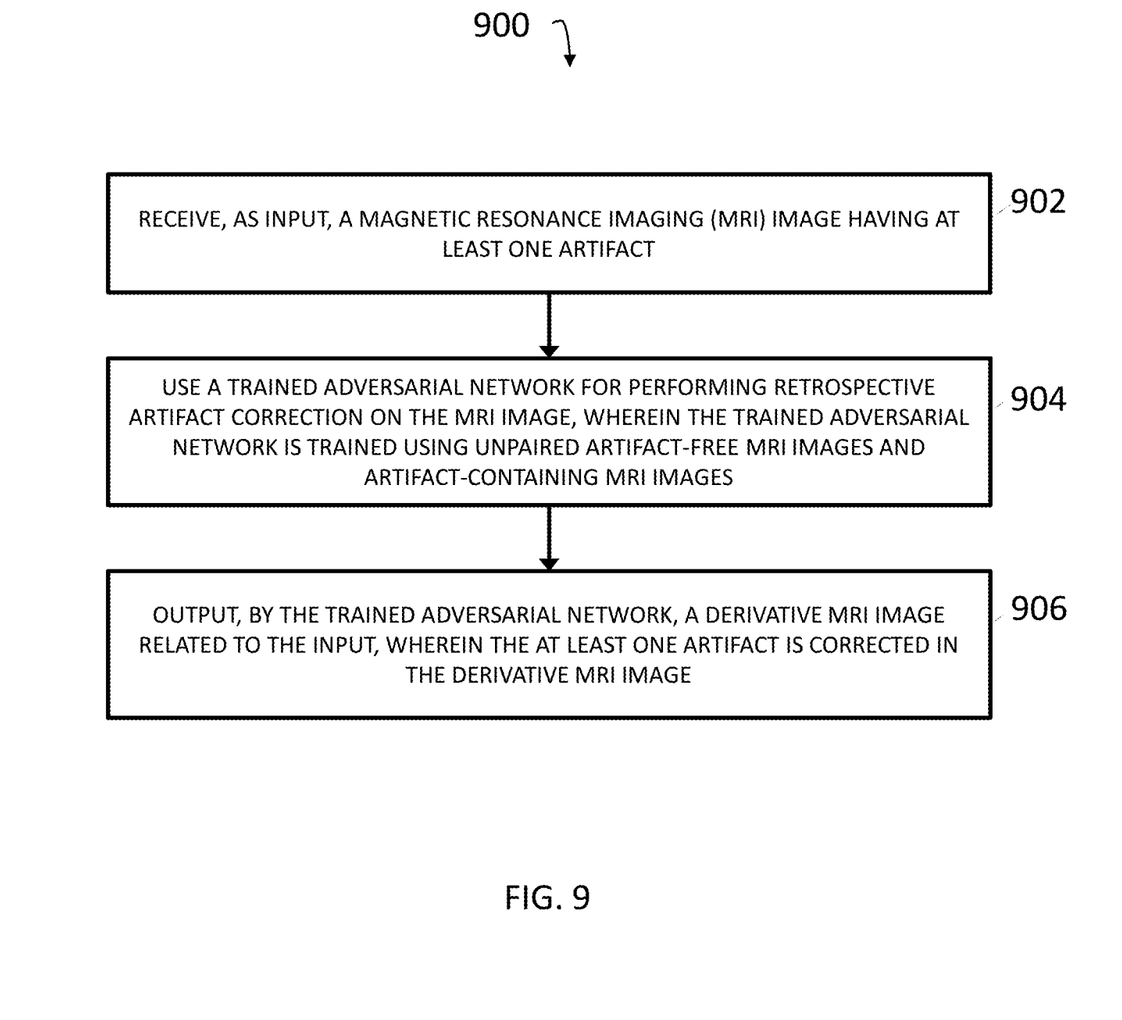
FIG. 9 is a flow chart illustrating an example process for using a trained adversarial network to perform retrospective MRI artifact correction.

FIG. 9 is a flow chart illustrating an example process for using a TAN 808 to perform retrospective MRI artifact correction. In some embodiments, process 900 described herein, or portions thereof, may be performed at or by system 800, computing platform(s) 802, TAN 808, and/or another module or device. For example, computing platform(s) 802 may include a mobile device, a computer, or other equipment (e.g., a medical device) and TAN 808 may include various deep learning based algorithms executing on computing platform(s) 802 for transforming or translating input (e.g., artifact-containing MRI images) into output (e.g., artifact-free MRI images). In some embodiments, process 900 may include steps 902-906.

In step 902, an MRI image having at least one artifact may be received as input. In some embodiments, the MRI image having at least one artifact may be a T1-weighted MRI image or a T2-weighted MRI image.

In step 904, a trained adversarial network may be used for performing retrospective artifact correction on the MRI image, wherein the trained adversarial network is trained using unpaired artifact-free MRI images and artifact-containing MRI images.

In some embodiments, the trained adversarial network may be trained using a first autoencoder for translating images of a first image domain to a second image domain and a second autoencoder for translating images of the second image domain to the first image domain.

In some embodiments, the first autoencoder may include a first artifact encoder for encoding artifact information associated with a first image of the first image domain and a first content encoder for encoding content information associated with a first image of the first image domain and wherein the second autoencoder may include a second artifact encoder for encoding artifact information associated with a first image of the second image domain and a second content encoder for encoding content information associated with a first image of the second image domain.

In some embodiments, the first autoencoder may include a decoder for decoding encoded content information and encoded artifact information into a second image of the first image domain or a second image of the second image domain.

In some embodiments, the encoded content information used by the decoder may be associated with the first image of the first image domain and wherein the encoded artifact information used by the decoder may be associated with the first image of the second image domain.

In some embodiments, the first image domain may represent a group of artifact-containing MRI images and the second image domain may represent a group of artifact-free MRI images.

In some embodiments, the trained adversarial network may be trained using a first discriminator for distinguishing a real image of the first image domain from an adversarial network generated image of the first image domain and a second discriminator for distinguishing a real image of the second image domain from an adversarial network generated image of the second image domain.

In some embodiments, the trained adversarial network may be trained using a pixel-wise consistency loss function for enforcing identity translation mapping, two least-squares loss functions for adversarial learning, or a multi-scale content consistency loss function based on pixel, low-level content features, and high-level content features between images.

In step 906, a derivative MRI image related to the input may be outputted by the trained adversarial network, wherein the derivative MRI image may be free of the at least one artifact.

It will be appreciated that process 900 is for illustrative purposes and that different and/or additional actions may be used. It will also be appreciated that various actions described herein may occur in a different order or sequence.

It should be noted that system 800, computing platform(s) 802, TAN 808, and/or functionality described herein may constitute a special purpose computing device. Further, system 800, computing platform(s) 802, TAN 808, and/or functionality described herein can improve the technological field of MRI processing and related MRI artifact correction. For example, by using one or more unsupervised training techniques, TAN 808 can be trained efficiently to identify and remove artifacts with remarkable efficacy from artifact-containing images to recover or generate artifact-free counterparts. Moreover, since TAN 808 is trained using one or more unsupervised training techniques, significant time and resources may be conserved since paired image sets (e.g., matching images with and without artifacts) are not needed and, as such, resources (e.g., time and effort) spent collecting and/or artificially generating such pairs are not required.

REFERENCES

The disclosure of each of the following references is incorporated herein by reference in its entirety to the extent not inconsistent herewith and to the extent that it supplements, explains, provides a background for, or teaches methods, techniques, and/or systems employed herein.

[1] Zhu, J., Gullapalli, R. P., MR artifacts, safety, and quality control. RadioGraphics 26, 275-297 (2006).
[2] Zaitsev, M., Maclaren, J. & Herbst, M. Motion artifacts in MRI: A complex problem with many partial solutions. Journal of Magnetic Resonance Imaging 42, 887-901 (2015).
[3] Zhu, J.-Y., Park, T., Isola, P., Efros, A. A. Unpaired image-to-image translation using cycle-consistent adversarial networks. IEEE International Conference on Computer Vision (ICCV) (2017).
[4] Isola, P., Zhu, J.-Y., Zhou, T., Efros, A. A. Image-to-image translation with conditional adversarial networks. IEEE Conference on Computer Vision and Pattern Recognition (CVPR), (2017).

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for performing retrospective magnetic resonance imaging (MRI) artifact correction, the method comprising:
   receiving, as input, a magnetic resonance imaging (MRI) image having at least one artifact;
   using a trained adversarial network for performing retrospective artifact correction on the MRI image, wherein the trained adversarial network is trained using unpaired artifact-free MRI images and artifact-containing MRI images, wherein the trained adversarial network is trained using a first autoencoder for translating images of a first image domain to a second image domain and a second autoencoder for translating images of the second image domain to the first image domain; and
   outputting, by the trained adversarial network, a derivative MRI image related to the input, wherein the at least one artifact is corrected in the derivative MRI image.

2. The method of claim 1 wherein the first autoencoder includes a first artifact encoder for encoding artifact information associated with a first image of the first image domain and a first content encoder for encoding content information associated with a first image of the first image domain and wherein the second autoencoder includes a second artifact encoder for encoding artifact information associated with a first image of the second image domain and a second content encoder for encoding content information associated with a first image of the second image domain.

3. The method of claim 1 wherein the first autoencoder includes a decoder for decoding encoded content information and encoded artifact information into a second image of the first image domain or a second image of the second image domain.

4. The method of claim 3 wherein the encoded content information used by the decoder is associated with the first image of the first image domain and wherein the encoded artifact information used by the decoder is associated with the first image of the second image domain.

5. The method of claim 1 wherein the first image domain represents a group of artifact-containing MRI images and the second image domain represents a group of artifact-free MRI images.

6. The method of claim 1 wherein the trained adversarial network is trained using a first discriminator for distinguishing a real image of the first image domain from an adversarial network generated image of the first image domain and a second discriminator for distinguishing a real image of the second image domain from an adversarial network generated image of the second image domain.

7. The method of claim 1 wherein the trained adversarial network is trained using a pixel-wise consistency loss function for enforcing identity translation mapping, two least-squares loss functions for adversarial learning, or a multi-scale content consistency loss function based on pixel, low-level content features, and high-level content features between images.

8. The method of claim 1 wherein the MRI image having at least one artifact is a T1-weighted MRI image or a T2-weighted MRI image.

9. A system for performing retrospective magnetic resonance imaging (MRI) artifact correction, the system comprising:
- at least one computing platform including at least one processor; and
- a trained adversarial network executable by the at least one processor for:
  - receiving, as input, a magnetic resonance imaging (MRI) image having at least one artifact;
  - using a trained adversarial network for performing retrospective artifact correction on the MRI image, wherein the trained adversarial network is trained using unpaired artifact-free MRI images and artifact-containing MRI images, wherein the trained adversarial network is trained using a first autoencoder for translating images of a first image domain to a second image domain and a second autoencoder for translating images of the second image domain to the first image domain; and
  - outputting, by the trained adversarial network, a derivative MRI image related to the input, wherein the at least one artifact is corrected in the derivative MRI image.

10. The system of claim 9 wherein the first autoencoder includes a first artifact encoder for encoding artifact information associated with a first image of the first image domain and a first content encoder for encoding content information associated with a first image of the first image domain and wherein the second autoencoder includes a second artifact encoder for encoding artifact information associated with a first image of the second image domain and a second content encoder for encoding content information associated with a first image of the second image domain.

11. The system of claim 9 wherein the first autoencoder includes a decoder for decoding encoded content information and encoded artifact information into a second image of the first image domain or a second image of the second image domain.

12. The system of claim 11 wherein the encoded content information used by the decoder is associated with the first image of the first image domain and wherein the encoded artifact information used by the decoder is associated with the first image of the second image domain.

13. The system of claim 9 wherein the first image domain represents a group of artifact-containing MRI images and the second image domain represents a group of artifact-free MRI images.

14. The system of claim 9 wherein the trained adversarial network is trained using a first discriminator for distinguishing a real image of the first image domain from an adversarial network generated image of the first image domain and a second discriminator for distinguishing a real image of the second image domain from an adversarial network generated image of the second image domain.

15. The system of claim 9 wherein the trained adversarial network is trained using a pixel-wise consistency loss function for enforcing identity translation mapping, two least-squares loss functions for adversarial learning, or a multi-scale content consistency loss function based on pixel, low-level content features, and high-level content features between images.

16. The system of claim 9 wherein the MRI image having at least one artifact is a T1-weighted MRI image or a T2-weighted MRI image.

17. A non-transitory computer readable medium having stored thereon executable instructions that when executed by at least one processor of at least one computer cause the at least one computer to perform steps comprising:
- receiving, as input, a magnetic resonance imaging (MRI) image having at least one artifact;
- using a trained adversarial network for performing retrospective artifact correction on the MRI image, wherein the trained adversarial network is trained using unpaired artifact-free MRI images and artifact-containing MRI images, wherein the trained adversarial network is trained using a first autoencoder for translating images of a first image domain to a second image domain and a second autoencoder for translating images of the second image domain to the first image domain; and
- outputting, by the trained adversarial network, a derivative MRI image related to the input, wherein the at least one artifact is corrected in the derivative MRI image.

* * * * *